US005795845A

United States Patent [19]

Yang et al.

[11] Patent Number: 5,795,845

[45] Date of Patent: Aug. 18, 1998

[54] METHOD FOR THE CONTROL OF WEEDS WITH WEAKLY VIRULENT OR NON-VIRULENT PLANT PATHOGENS

[75] Inventors: Shaw-Ming Yang, Frederick, Md.; William Minor Dowler, Clemson, S.C.; Norman Werth Schaad, Myersville, Md.; William Joseph Connick, Jr., New Orleans, La.

[73] Assignee: The United States of America as represented by the Secretary of Argiculture, Washington, D.C.

[21] Appl. No.: 785,635

[22] Filed: Jan. 17, 1997

[51] Int. Cl.[6] ..................... A01N 63/00

[52] U.S. Cl. ..................... 504/117

[58] Field of Search ..................... 504/117

[56] References Cited

U.S. PATENT DOCUMENTS 4,902,333 2/1990 Quimby, Jr. ..................... 71/79

OTHER PUBLICATIONS

Amsellem et al. "Abolition of Selectivity of Two Mycoherbicidal Organisms and Enhanced Virulence of Avirulent Fungi by an Invert Emulsion". *Phytopathology*. 81(9):985–988. 1991.

Womack et al. "Mycoherbicide Formulation and the Potential for Bracken Control". *Pesticide Science*. 37:337–341. 1993.

Connick, Jr. et al. "An Improved Invert Emulsion with High Water Retention for Mycoherbicide Delivery". *Weed Technology*. 5(2):442–444. 1991.

*Primary Examiner*—S. Mark Clardy

*Attorney, Agent, or Firm*—M. Howard Silverstein; John Fado; Janelle S. Graeter

[57] ABSTRACT

A bioherbicidal composition comprising an invert emulsion carrier and a microorganism which is a non- or weakly-virulent pathogen in the absence of the carrier is useful as a herbicidal agent when the microorganism is present in an amount effective for herbicidal activity to occur in the presence of the carrier.

13 Claims, No Drawings

METHOD FOR THE CONTROL OF WEEDS WITH WEAKLY VIRULENT OR NON-VIRULENT PLANT PATHOGENS

BACKGROUND OF THE INVENTION

1. Field of the Invention

Biologically active fungal plant pathogens have been used successfully as bioherbicides, and carriers have been employed for the application of these pathogens as herbicides in order to enhance their efficacy as well as to improve application efficiency and ease. The search has continued, however, for improved broad-spectrum formulations which are both safe and effective. This invention relates to the use of weakly- or non-virulent microorganisms used in combination with invert emulsion carriers for the biological control of weeds.

2. Description of the Prior Art

Fungal plant pathogens have been shown to achieve effective control of round-leaf mallow (*Malva pusilla* Sm.) in Canada (Makowski and Mortensen. 1992. *Proceedings of the First International Weed Control Conaress II*, pp. 298–300), strangler vine [*Morrenia odorata* (H. & A.) Lindl.] in citrus groves in Florida [Ridings et al. 1976. In *Proceedings IV International Symposium on Biological Control of Weeds*, T. E. Freeman (ed.) pp. 224–240] and jointvetch [*Aeschynomene virginica* (L.) B.S.P.] in rice and soybeans in Arkansas, Louisiana and Mississippi (Smith. 1986. *Weed Science*. vol. 34, suppl. 1, pp. 17–23). Promising candidates have also been found for the control of hemp sesbania [*Sesbania macrocarpa* Muhl.=*S. exaltata* (Raf.) Rydb. ex A. W. Hill] in Mississippi and dodder (Cuscuta spp.) on soybeans [Glycine max (L.) Merr.] in China (Gao and Gam. 1992. *Chinese Journa of Biological Control*. vol. 8, pp. 173–175).

Limitations in host specificity and in formulations used in current bioherbicide methods have been noted [Auld and Morin. 1995. *Weed Technology*. vol. 9, pp. 638–652; Charudattan, R. 1991. In *Microbial Control Of Weeds*, D. O. TeBeest (ed.), pp. 25–57, Chapman and Hall, New York; Munyaradzi et al. 1990. *Aspects of Applied Biology*. vol. 24, pp. 169–178], however, and efforts have continued for the development of broad-spectrum biological control agents that work only where applied.

SUMMARY OF THE INVENTION

We have discovered that non- or weakly-virulent pathogenic microorganisms in combination with invert emulsion carriers are useful compositions to achieve effective broad-spectrum bioherbicidal activity, i.e. to control weeds.

In accordance with this discovery, it is an object of the invention to provide a novel, effective bioherbicidal composition comprising a non- or weakly-virulent pathogenic microorganism and an invert emulsion carrier.

It is another object of the invention to provide a method of controlling weeds by applying the novel bioherbicidal composition to targeted weeds in amounts effective to damage or kill the weeds.

Other objects and advantages of the invention will become readily apparent from the following description.

DETAILED DESCRIPTION OF THE INVENTION

The potential of weakly pathogenic and saprophytic isolates of Myrothecium as safe, broad-spectrum bioherbicides for weed control was investigated. Broad-spectrum, as opposed to target-specific, bioherbicides are advantageous with respect to wider market potential, increased commercial interests for development and marketing and ease of application by homeowners and farmers. A major disadvantage of broad-spectrum bioherbicides, however, is the possibility of infecting and damaging non-target plant species which may be in the vicinity of the targeted weeds, thus posing environmental risks. This disadvantage can be overcome by using non- or weakly-virulent pathogens in combination with special formulated carriers because the organisms require the presence of carrier to infect the target weed. By utilizing such a combination, the bioherbicide can be directed to the specific site of the target weed and thus reduce the potential for harming desirable plants.

Non-virulent pathogens (or saprophytes) are microorganisms which grow on the host but are not pathogenic to the host. Weakly-virulent pathogens are microorganisms which can infect plants and may produce lesions, but do not cause severe damage or kill the plants. It has been found that these pathogens become highly virulent and severely damage or kill target plants when applied to the plants in an invert emulsion (water-in-oil) carrier. Studies were thus undertaken to determine the effectiveness of using saprophytic fungi as broad-spectrum bioherbicides for control of weeds. Greenhouse studies showed that three isolates of Myrothecium spp. were at most only weakly virulent on redroot pigweed, plumeless thistle, velvetleaf and groundcherry following inoculation with conidia in a sucrose-Tween 20 (ST) solution and treatment with dew at 30° C. for 18 to 24 hours. Without dew, however, conidia of all three isolates inoculated in the invert emulsion (IE) carrier caused severe damage or death to each of the four weeds. Velvetleaf was severely damaged by only one of the three isolates in the carrier and without dew. The carrier alone caused only slight injury at most.

Field tests indicated that the three isolates with carrier killed redroot, pigweed and plumeless thistle but only slightly damaged groundcherry and velvetleaf.

Myrothecium spp. are worldwide in distribution and normally not pathogenic (Domsch et al. 1980. *Compendium of Soil Fungi*. vol. 1. Academic Press, New York; Farr et al. 1989. *Fungi on Plants and Plant Products in the United States*. American Phytopathological Society, St. Paul, Minn.). Furthermore, *M. verrucaria* is a weak competitor in soil, has limited survival in plant residue, does not spread from diseased plants to healthy plants, and alone (i.e. without the IE carrier) requires a high inoculum threshold to infect, killing weeds without dew only when applied with the carrier (Martin et al. 1959. *Proceedings of Soil Science society of America*. vol. 23, pp. 217–220; Yang and Jong. 1995. *Plant Disease*. vol. 79, pp. 998–1002). Weakly- and non-pathogenic isolates of Myrothecium were thus selected to serve as models for efficacy studies.

Two isolates of *Myrothecium verrucaria* (Albert. & Schwein.) Ditmar:Fr. (*M. verrucaria*) and one isolate of *M. roridum* Tode:Fr. were weakly to non-virulent on redroot pigweed, plumeless thistle, velvetleaf and groundcherry when the plants were inoculated with conidial suspensions in a ST solution and incubated in a dew chamber at 30° C. for 18 to 24 hr. Each of the three isolates severely damaged or killed all individuals of redroot pigweed, plumeless thistle and groundcherry, but only the *M. roridum* isolate severely damaged velvetleaf without dew when the plants were sprayed with the carrier plus conidia. Carrier alone caused slight or no injuries.

TABLE 1

Effect of a specially formulated invert emulsion (IE) carrier and dew on virulence and host range of three isolates of Myrothecium spp. in greenhouse tests[a].

| Myrothecium isolate | IE[b] | Dew[c] | Redroot pigweed[d] | Plumeless thistle[d] | Velvetleaf[d] | Groundcherry[d] |
|---|---|---|---|---|---|---|
| 1 | – | – | 0[e] | 0 | 0 | 0 |
| 2 | – | – | 0 | 0 | 0 | 0 |
| 3 | – | – | 0 | 0 | 0 | 0 |
| 1 | – | + | 1 | 0 | 1 | 0 |
| 2 | – | + | 0 | 0 | 0 | 0 |
| 3 | – | + | 2 | 1 | 0 | 0 |
| 1 | + | – | 4 | 4 | 2 | 3 |
| 2 | + | – | 4 | 4 | 2 | 4 |
| 3 | + | – | 4 | 4 | 2 | 3 |

[a]Plants sprayed with the specially formulated carrier only sustained, at most slight damage (data not shown). Plants were four weeks old at inoculation (4 to 6 true leaf stage). Concentration of conidia was $1 \times 10^8$/ml.
[b]IE = Invert Emulsion carrier "–" = no IE, conidia applied in solution of sucrose (2%) and Tween 20 (0.1%). "+" = conida applied in IE.
[c]"+" = plants given dew at 30° C. for 18–24 hours. "–" no dew provided; plants placed directly on greenhouse bench after inoculation (17–33° C., 40–70% RH).
[d]Redroot pigweed (*Amaranthus retroflexus*, Amaranthaceae); plumeless thistle (*Carduus acanthoides*, Asteraceae); velvetleaf (*Abutilon theophrastii*, Malvaceae); and groundcherry (*Physalis ixocarpa*, Solanaceae).
[e]0 = no damage, 1 and 2 = slight damage, 3 = severe damage, 4 = plants dead.

Bioherbicidal activity of the three isolates for the four weeds were tested in the field. The three isolates killed redroot pigweed and plumeless thistle but only slightly damaged groundcherry and velvetleaf.

Three isolates of Myrothecium in ST solution did not infect the plants in this study without dew and only caused slight damage, at most, when a dew period was provided (see Table 1). Except for velvetleaf, severe damage or death occurred without dew only when plants were inoculated with conidia in the IE carrier. For velvetleaf, two isolates in the IE carrier caused slight damage to velvetleaf without dew; a third required dew plus the IE carrier, and then it caused only slight damage.

Field inoculations confirmed greenhouse results that the three isolates could kill redroot pigweed and plumeless thistle when applied in IE carrier. Only slight damage to velvetleaf and Mexican groundcherry occurred in the field, however, despite severe damage to groundcherry in the greenhouse.

Results from this study with Myrothecium spp., and from others with Alternaria spp. (Amsellem et al. 1990; Yang et al. 1993.) have thus provided support for the utilization of saprophytic or weakly-pathogenic fungi in combination with an IE carrier for use as broad-spectrum bioherbicides.

Additional field studies confirmed the results of greenhouse studies that non-virulent isolates of *M. verrucaria* in IE carrier kill weeds including amaranth, plumeless thistle, Italian thistle, and lamb's quarters (Table 2).

Field tests conducted during May (Table 3), June (Table 4), July (Table 5) and September (Table 6) showed that a weakly virulent isolate of *Alternaria angustiovoidea* also kills shoots of leafy spurge. The high number of dead or injured shoots in the July and September ST, check and IE only plots was attributed to the high temperatures occurring at that time.

Additional studies were carried out to evaluate the efficacy of *M. verricaria* for control of weeds in mixed weed fields. Results showed that the fungus in combination with the IE carrier effectively controlled lamb's quarters, Rumex sp. and *Portulaca oleraceae* (Table 7).

TABLE 2

Virulence and host range of *M. verrucaria* when tested in an invert emulsion (IE) carrier under field conditions.

| | Treatments[b] | | | |
|---|---|---|---|---|
| Weed species[a] | Isolate ATCC 18398 in IE | Isolate ATCC 13667 in IE | IE | Isolate ATCC 18398 in ST |
| 1 | 4.0 (4.0)[d] | 4.0 (4.0) | 0.4 (0)*[e] | 0 (0)* |
| 2 | 4.0 (4.0) | 4.0 (4.0) | 0 (0)* | 0 (0)* |
| 3 | 4.0 (4.0) | 4.0 (4.0) | 0 (0) | 0 (0) |
| 4 | 1.0 (0.8) | 0 (0) | 0 (0) | 0 (0) |
| 5 | 4.0 (4.0) | 4.0 (4.0) | 0 (0) | 0 (0) |
| 6 | 2.6 (2.4) | 2.0 (0.8) | 1.0 (0) | 0 (0) |
| 7 | 4.0 (2.4) | 4.0 (2.4) | 0 (0) | 0 (0) |
| 8 | 3.0 (0)* | 1.8 (0.4)* | 1.0 (0) | 0 (0)* |
| 9 | 2.4 (0)* | 2.2 (0)* | 1.6 (0)* | 0 (0)* |
| 10 | 0.4 (2.2) | 3.6 (3.2) | 1.8 (0.8) | 0 (0) |
| 11 | 2.4 (3.2 | 1.2 (0.4) | 0 (0) | 0 (0) |

[a]Weed species: 1. Redroot pigweed (*Amanranthus retroflexus*, Amaranthaceae); 2. Plumeless thistle (*Carduus acanthoides*); 3. Italian thistle (*Carduus pycnocephalus*); 4. Spotted knapweed (*Centaurea maculosa*, Asteraceae); 5. Lamb's quarters (*Chenopodium album*, Chenopodiaceae); 6. Cowpea (*Vigana unguiculata*, Fabaceae); 7. Field bindweed (*Convolvulus arvensis*); 8. ivyleaf morninglory (*Ipomoea hederacea*); 9. Tall morninglory (*Ipomoea purpurea*, Convolvulaceae); 10. Velvetleaf (*Abutilon theophrastii*, Malvaceae); 11. Mexican groundcherry (*Physalis ixocarpa*, Solanaceae).
[b]Plants were sprayed with 400 ml of inoculum containing $1 \times 10^{10}$ spores/ml on in IE carrier, IE alone or in ST solution.
[d]Disease index = summation of severity rating value x number of plants with that rating/total number of plants. 0 = no visible lesions; 1 = small scattered lesions; 2 = numerous lesions coalesced; 3 = 75% of leaves dead or defoliated; 4 = dying or dead plant. Disease severity was rated two and four (in parenthses) weeks after spraying.
[e]*indicates plant blooming.

TABLE 3

Virulence of spores of *Alternaria angustiovoidea* in a solution of sucrose-Tween 20 (ST) or invert emulsion (IE) carrier to leafy spurge.

| | Treatment[a] | | | | |
|---|---|---|---|---|---|
| Replication | ST | Spores in ST | IE | Spores in IE | CK |
| 1 | 0/252[b] | 0/94 | 1/56 | 19/30 | 0/134 |
| 2 | 0/187 | 0/226 | 33/44 | 12/16 | 0/99 |
| 3 | 0/119 | 0/211 | 0/52 | 8/9 | 0/97 |
| 4 | 0/99 | 0/95 | 13/20 | 11/16 | 0/100 |
| Total | 0/657 | 0/626 | 47/172 | 50/71 | 0/430 |
| % if dead or injured shoots/plot | 0 | 0 | 27.3 | 70.4 | 0 |

[a]Plants were sprayed with sucrose (0.5%)-Tween 20 (0.1%) solution; IE equal mixture of oil phase (80 ml Sunspray 6N, 20 ml mineral oil, 2 ml Myverol distilled monoglycerides 18-92) and water phase (Sucrose-Tween 20); or CK, no treatment and numbers of injured or dead and healthy shoots/plot. The final concentration of spores was $1 \times 10^5$/ml.
[b]Number of dead or injured shoots/total number of shoots in the plot (one meter row plot).

TABLE 4

Virulence of spores of *Alternaria angustiovoidea* in a solution of sucrose-Tween 20 (ST) or invert emulsion (IE) carrier to leafy spurge.

| | Treatment[a] | | | | |
|---|---|---|---|---|---|
| Replication | ST | Spores in ST | IE | Spores in IE | CK |
| 1 | 9/194[b] | 3/118 | 118/214 | 116/127 | 0/238 |
| 2 | 0/329 | 36/396 | 42/344 | 223/231 | 0/217 |
| 3 | 0/228 | 27/363 | 49/147 | 120/128 | 0/436 |
| 4 | 0/229 | 0/160 | 56/89 | 154/206 | 0/199 |

TABLE 4-continued

Virulence of spores of *Alternaria angustiovoidea* in a solution of sucrose-Tween 20 (ST) or invert emulsion (IE) carrier to leafy spurge.

| | Treatment[a] | | | | |
|---|---|---|---|---|---|
| Replication | ST | Spores in ST | IE | Spores in IE | CK |
| Total | 9/980 | 66/1037 | 265/794 | 613/692 | 0/1090 |
| % of dead or injured shoots/plot | 0.9 | 6.4 | 33.4 | 88.6 | 0 |

[a]Plants were sprayed on June 23, and numbers of injured or dead and healthy shoots/plot counted on July 10. The final concentration of spores was $1 \times 10^5$/ml
[b]As Table 3.

TABLE 5

Virulence of spores of *Alternaria angustiovoidea* in a solution of sucrose-Tween 20 (ST) or invert emulsion (IE) carrier to leafy spurge.

| | Treatment[a] | | | | |
|---|---|---|---|---|---|
| Replication | ST | Spores in ST | IE | Spores in IE | CK |
| 1 | 1/118[b] | 2/65 | 20/52 | 25/29 | 4/106 |
| 2 | 9/67 | 10/178 | 62/95 | 37/66 | 7/61 |
| 3 | 7/138 | 9/108 | 21/60 | 4/5 | 0/117 |
| 4 | 29/125 | 13/100 | 18/27 | 11/26 | 82/155 |
| Total | 46/448 | 34/451 | 121/234 | 77/126 | 93/439 |
| % of dead or injured shoots | 10.3 | 7.6 | 51.7 | 61.1 | 21.2 |

[a]Plants were sprayed as described in Table 3 on July 27, and number of dead or injured and healthy shoots were counted on August 24.
[b]As Table 3.

TABLE 6

Virulence of spores of *Alternaria angustioboidea* in a solution of sucrose-Tween 20 or invert emulsion carrier to leafy spurge.

| | Treatment[a] | | | | |
|---|---|---|---|---|---|
| Replication | ST | Spores in ST | IE | Spores in IE | CK |
| 1 | 13/86[b] | 2/29 | 18/22 | 10/10 | 6/84 |
| 2 | 11/75 | 8/95 | 39/56 | 7/15 | 2/27 |
| 3 | 16/70 | 0/39 | 20/58 | 19/19 | 1/44 |
| 4 | 49/87 | 19/52 | 7/7 | 15/17 | 5/74 |
| Total | 79/318 | 29/215 | 84/143 | 51/61 | 14/229 |
| % of dead or injured shoots/plot | 24.8 | 13.5 | 58.7 | 83.6 | 6.1 |

[a]Plants were sprayed on September 13 and number of dead or injured and healthy shoots were counted on October 25.
[b]As Table 3.

TABLE 7

Severity of weeds in the test plots infected by *Myrothecium verrucaria*.

| | | No infection | Infection | |
|---|---|---|---|---|
| Treatment | Weed species | (%) | Slight | Severe |
| Invert emulsion + *M. verrucaria* | Cal[b] | 27 | 6 | 73 |
| | Pol | 13 | 41 | 46[c] |
| | Lfi | 24 | 50 | 26[c] |
| | Rumex sp. | 8 | | 92[c] |
| | Sni | 100 | | |
| | She | 100 | | |

TABLE 7-continued

Severity of weeds in the test plots infected by *Myrothecium verrucaria*.

| | | No infection | Infection | |
|---|---|---|---|---|
| Treatment | Weed species | (%) | Slight | Severe |
| Invert emulsion only | Cal[b] | 100 | | |
| | Pol | 61 | 39 | |
| | Lfi | 47 | 53 | |
| | Rumex sp. | 56 | 44 | |
| | Sni | 100 | | |
| | She | 100 | | |
| Sucrose-Tween 20 (ST) solution | Cal[b] | 100 | | |
| | Pol | 100 | | |
| | Lfi | 100 | | |
| | Rumex sp. | 100 | | |
| | Sni | 100 | | |
| | She | 100 | | |
| ST + *M. verrucaria* | Cal[b] | 100 | | |
| | Pol | 100 | | |
| | Lfi | 100 | | |
| | Rumex sp. | 100 | | |
| | Sni | 100 | | |
| | She | 100 | | |

[a]Average of 4 plots. Each plot is 1 $m^2$.
[b]Cal = *Chenopodium album*, Pol = *Portulaca oleraceae*, Lfi = *Leptochloa filiromis*, Sni = *Solanum nigrum*, She = *Sida hederacea*.
[c]Include 7, 8, and 42% of *P. oleraceae*, *L. filiromis* and Rumex killed, respectively.

Results from these studies have thus provided support for the utilization of saprophytic or weakly-pathogenic fungi in combination with an IE carrier for use as broad-spectrum bioherbicides.

In order to ensure that application of the bioherbicidal composition did not damage non-targeted plants in the vicinity of the target plants (or weeds), experiments were carried out to test for drift (as described in Experiment 3). Results showed that no evidence was found of damage to plants in subplots adjacent to those sprayed with the bioherbicide. If drift does occur, it is apparently negligible because no weeds in the adjacent subplots were injured.

Weakly- or non-virulent microorganisms which are useful in the bioherbicidal composition may easily be determined by one of ordinary skill in the art by carrying out the following steps: 1) determine weak or no pathogenicity of the a microorganism to targeted plants, 2) combine the potential microorganism with an IE carrier to prepare a microorganism/carrier composition and 3) determine the pathogenicity of the composition against the targeted plants. Effective microorganisms include weakly- or non-pathogenic isolates of bacteria such as Clavibacter, Corynebacterium, Pseudonomas, Xanthomonas and fungi such as Alternaria, Cladosporium, Myrothecium, Penicillium, Phoma and Stemphylium. Preferred isolates are *Myrothecium verrucaria, Myrothecium leucotricum, Myrothecium roridum, Alternaria angustiovoidea* and *Alternaria alternata*. Particularly preferred are *Myrothecium verrucaria* and *Myrothecium roridum.*

The IE carrier is a water-in-oil emulsion (1:1, v/v) which includes an oil phase of mineral or vegetable oil, a horticultural oil such as Sunspray 6N, and an emulsifier such as a distilled monoglyceride emulsifier such as Myverol 18-92 or Myvacet 9-45 (both from Eastman Chemical Co., Kingsport, Tenn. 37662), and a water phase of distilled or tap water, sucrose and Tween 20 (J. T. Baker, Phillipsburg, N.J. 08665). Sunspray 6N [Sun Company, Inc. (R & M), Tenn. Penn Center, 1801 Market St. Philadelphia, Pa. 19103] is a horticultural spray oil used in the formulation of insecticides, and its active ingredient is 100% refined petroleum distillate (at least 92% unsulfonated residue of petroleum distillate). While the composition of the emulsion may vary somewhat according to normal optimization procedures, an effective formulation has been found to contain about 20 ml mineral or vegetable oil (20%, v/v), about 80 ml Sunspray 6N (80%, v/v), about 1–2 ml emulsifier, about 100 ml water, about 0.5 to about 2 g sucrose and about 1 ml Tween 20.

The emulsion is prepared by mixing the oil phase components and water (or aqueous) phase components separately, then combining in equal parts and shaking for a time sufficient for an emulsion to form. The non- or weakly-virulent pathogens are present in amounts effective for controlling the particular targeted plant, and these amounts may vary according to the identity of the targeted plant and the pathogen used. A final concentration of at least about $10^8$ conidia/ml of Myrothecium spp. or at least about $10^4$ conidia/ml of Alternaria spp. has been found effective.

The bioherbicidal composition may be applied to target plants by any conventional method including an atomizer, a crown spray-tool, a garden sprayer or a squeeze bottle. Application amounts may vary according to the kind and density of target plant. An amount of about 75 ml/m$^2$ has been found effective.

Targeted plants which have been successfully controlled by application of the bioherbicidal composition include redroot pigweed, plumeless thistle, Italian thistle, velvetleaf, groundcherry, hemp sesbania, common cocklebur, amaranth, Lamb's quarters, leafy spurge, Rumex sp., Portulaca oleraceae and spiny pigweed.

The following examples are intended only to further illustrate the invention and are not intended to limited the scope of the invention as defined by the claims.

EXAMPLES

Example 1

Preparation of Bioherbicidal Composition

Three isolates of Myrothecium spp. were grown on potato-dextrose-agar supplemented with 30 mg/L penicillin G and 100 mg/L streptomycin sulphate (PSPDA) at 25° C. (12 hour light 40 $\mu$E.s$^{-1}$m$^2$). After 6 to 8 weeks, conidia of each isolate were collected by flooding the cultures with a sucrose-Tween (ST) solution (2 g sucrose, 100 ml tap water and 0.1 ml Tween 20) and rubbing the surface with a rubber spatula. The stock conidial suspension was filtered through two layers of cheesecloth and adjusted to $2\times10^8$ conidia/ml with ST by using a hemocytometer.

Inoculum was stored in ST solution to maintain viability of conidia and to avoid possible plugging of the sprayer. Although most conidia of *M. verrucaria* isolate ATCC 90310 had settled to the bottom of the container after storage in ST solution at 4° C. for 14 months, they remained virulent, and no germinated conidia were found. Ninety-three and 82% of conidia (average of two tests) stored for 1 and 14 months, respectively, germinated after two drops of spore suspensions were placed on potato-dextrose agar plates for 8 hr. Conidia which had been stored for three months (June 21 to September) resulted in rates of 95% germination on water agar supplemented with 2% sucrose. A 100% rate of infection was still observed with 4-week-old or younger bindweed plants.

A water in oil invert emulsion (IE) carrier was prepared by mixing an equal amount of oil phase with the ST solution (1:1, v/v) and shaking until an emulsion was formed. The oil phase contained 20 ml mineral oil, 80 ml Sunspray 6N and 1–2 ml emulsifier.

Example 2

Determination of Effects of Bioherbicidal Composition

Seeds of redroot pigweed (*Amaranthus retroflixus* L.), plumeless thistle (*Carduus acanthoides* L.), velvetleaf (*Abutilon theophrastii* Medik.) and groundcherry (*Physalis ixocarpa* L.) were planted in a pasteurized greenhouse soil mix |sand, limestone, fertilizer (10-10-10), AquaGrow "G" granular and vermiculite) in 10-cm clay pots (Yang and Jong. 1995. *Plant Disease*. vol. 79. pp. 994–997). Four weeks after planting (4 to 6 true leaf stage), 10 pots of each plant species (40 pots total) were randomly placed within a 1-m$^2$ area and treated either with 100 ml ST plus conidia, IE alone or IE plus conidia, using a 3.785-liter garden sprayer with a T-Jet 8002 nozzle (spraying System Co., Wheaton, Ill.). The plants then were placed directly on greenhouse benches (17°–28° C., 50–70% RH) . In addition, 10 pots of each plant species were sprayed with ST plus conidia of each isolate, placed in dew chambers at 30° C. for 18 to 24 hours, then placed on greenhouse benches. This experiment was repeated two times.

A field test also was run to determine bioherbicidal activity of each isolate against redroot pigweed, plumeless thistle, velvetleaf and Mexican groundcherry. Three-week-old seedlings in Jiffy pots, one plant per pot, were transplanted into the field plots. Plots were 2 m×1.5 m with four rows each 32 cm apart and 2 m long. Of each species, there were five plants per row. Plants were watered at transplanting and weekly thereafter. Inoculations were made three weeks after transplanting by spraying the plot with 150 ml of IE plus conidia ($1\times10^{10}$) using the garden sprayer described above. A plot sprayed with IE only served as a control. The temperature, relative humidity and wind speed during spraying were 28°–35° C., 24–40% and 10–12 mph, respectively. The temperature and relative humidity during the four weeks after inoculation were 15°–33° C. and 30–100%, respectively.

Disease severity was rated four weeks after inoculation. An 0–4 numerical system was used to rate the severity where 0=no infection; 1=less than 25% of leaf area damaged; 2=26–50% of leaf area damaged; 3=51–75% of leaf area damaged or growing points killed although leaves still green; 4—plants dead. A disease index score was then calculated from each test by summation of (severity rating x number of plants in that rating)/total number of plants. Average disease indices (rounded off to the nearest whole number) from the three tests are shown in Table 1. An average disease index (DI) of 1 is considered no damage, an average DI of 1 or 2 indicates slight damage, and average DI of 3 indicates severe damage and an average DI of 4 means the plants are dead.

Example 3

Determination of Drift

Two plots (1 m×1 m) of plumeless thistle and one plot (1 m× 1 m) of common cocklebur (*Xanthium strumarium*) were used for testing the drift of *M. verrucaria* in the field. Each plot had 6 rows, 20 cm apart, 1 m long. Each row contained 6 plumeless thistle or 3 cocklebur plants. The plots were spaced 30 cm apart and were divided into two subplots with 3 rows each. One subplot of plumeless thistle was sprayed with 100 ml ST solution and the other with 100 ml *M. verrucaria* isolate ATCC 18398 (S-1) adjusted to contain $10^8$ conidia/ml in IE carrier using a one-gallon sprayer. The spray nozzle was held 30–40 cm above the plots during application. One subplot of the second plot of plumeless thistle was sprayed with 100 ml IE and the other with 100 ml S-1 inoculum in ST. One subplot of cocklebur was sprayed with 100 ml IE and the other with 100 ml S-1 inoculum in IE. The temperature, relative humidity and windspeed during spray were 28°–34° C., 24–32% and 10 mph, respectively.

Results were recorded four weeks after inoculation. All plumeless thistle or cocklebur plants sprayed with IE containing S-1 inoculum were severely infected or killed. No symptoms were found on plants in the adjacent subplots sprayed with IE alone, ST or S-1 in ST. some young volunteer Canada thistle (*Cirsium arvense*) plants in the subplots sprayed with IE containing S-1 were also killed.

We claim:

1. A bioherbicidal composition comprising an invert emulsion carrier, and a microorganism which is a non- or weakly-virulent pathogen in the absence of said carrier, said microorganism being present in an amount effective for herbicidal activity to occur in the presence of said carrier.

2. The composition of claim 1, wherein said pathogenic microorganism is a weakly- or non-pathogenic bacterium or a weakly- or non-pathogenic fungus.

3. The composition of claim 2, wherein said bacterium is an isolate of Clavibacter, Corynebacterium, Pseudomonas or Xanthomonas.

4. The composition of claims 2, wherein said fungus is an isolate of Alternaria, Cladosporium, Myrothecium, Penicillium, Phoma and Stemphylium.

5. The composition of claim 4, wherein said isolate is *Myrothecium verrucaria* or *Myrothecium roridum*.

6. The composition of claim 1, wherein said invert emulsion comprises an oil phase of mineral or vegetable oil, a horticultural oil and an emulsifier and an aqueous phase of water, sucrose and a surfactant, and said oil and said aqueous phases are present at a 1:1 ratio (v/v).

7. The composition of claim 6, wherein said horticultural oil is Sunspray 6N.

8. The composition of claim 6, wherein said emulsifier is a monoglyceride emulsifier.

9. The composition of claim 6, wherein said mineral or vegetable oil is about 20% (v/v), said horticultural oil is about 80% (v/v), said emulsifier is about 1 to about 2% and said aqueous phase contains about 0.5% to about 2% sucrose (w/v) and about 1% surfactant.

10. The composition of claim 4, wherein said Alternaria is present in an amount of at least about $10^4$ conidia/ml.

11. The composition of claim 4, wherein said Myrothecium is present in an amount of at least about $10^8$ conodia/ml.

12. A method of controlling weeds, said method comprising applying the bioherbicidal composition of claim 1 in an amount effective to kill or damage said weeds.

13. The method of claim 12, wherein said composition is applied in an amount of about 75 $ml/m^2$.

* * * * *